(12) United States Patent
Peinado et al.

(10) Patent No.: US 7,243,237 B2
(45) Date of Patent: Jul. 10, 2007

(54) SECURE COMMUNICATION WITH A KEYBOARD OR RELATED DEVICE

(75) Inventors: Marcus Peinado, Bellevue, WA (US); Josh Benaloh, Redmond, WA (US)

(73) Assignee: Microsoft Corporation, Redmond, WA (US)

(*) Notice: Subject to any disclaimer, the term of this patent is extended or adjusted under 35 U.S.C. 154(b) by 817 days.

(21) Appl. No.: 10/428,675

(22) Filed: May 2, 2003

(65) Prior Publication Data

US 2004/0230805 A1   Nov. 18, 2004

(51) Int. Cl.
    *H04L 9/00* (2006.01)
(52) U.S. Cl. .................................... 713/181; 726/2
(58) Field of Classification Search ............ 713/1, 713/2, 188, 194, 181; 380/200, 201, 255, 380/277; 726/2
See application file for complete search history.

(56) References Cited

U.S. PATENT DOCUMENTS

| | | | | |
|---|---|---|---|---|
| 4,386,266 | A |   | 5/1983 | Chesarek ............... 235/380 |
| 5,748,888 | A | * | 5/1998 | Angelo et al. ............. 726/26 |
| 5,870,723 | A | * | 2/1999 | Pare et al. ............... 705/39 |
| 5,892,900 | A |   | 4/1999 | Ginter et al. |
| 7,110,986 | B1 | * | 9/2006 | Zajkowski et al. .......... 705/64 |
| 2002/0080967 | A1 | * | 6/2002 | Abdo et al. ............. 380/270 |
| 2003/0005300 | A1 | * | 1/2003 | Noble et al. ............ 713/172 |
| 2003/0159053 | A1 | * | 8/2003 | Fauble et al. ............ 713/189 |

OTHER PUBLICATIONS

Desmedt, Y., "Computer Security by Redefining What a Computer Is", *ACM*, 1993, 160-166.
Papas, G.G., "Cryptographic Communication Key Entry Unit", *IBM Technical Disclosure Bulletin*, 1983, 26(5), 2387-2388.
Papas, G.G., "Encryption Pin Pad", *IBM Technical Disclosure Bulletin*, 1983, 26(5), 2393-2397.
Treat, D. G., "Keyboard Encryption", *IEEE Potentials*, 2002, 21(3), 40-42.

* cited by examiner

*Primary Examiner*—Kim Vu
*Assistant Examiner*—Joseph Pan
(74) *Attorney, Agent, or Firm*—Woodcock Washburn LLP

(57) ABSTRACT

Secure communication between a keyboard and a component, such as a piece of software running on a computer. A first initial value is known to both the keyboard and the component. The keyboard and the component exchange nonces. The keyboard and the component each compute a second initial value and a third initial value based on the nonces and the first initial value. Both the keyboard and the component perform the same computation, so that the keyboard and the component each have the same second and third initial values. The keyboard encrypts keystrokes destined for the component using CBC-3DES based on the key and the second initial value, and also creates a message authentication code for each keystroke using CBC-3DES-MAC based on the key and the third initial value. The component decrypts and verifies the keystrokes using the key and the second and third initial values.

22 Claims, 4 Drawing Sheets

SECURE COMMUNICATION WITH A KEYBOARD OR RELATED DEVICE

FIELD OF THE INVENTION

The present invention relates generally to the field of computer security. More particularly, the invention relates to the secure use of a keyboard over a communication channel that may be subject to interception or other types of tampering.

BACKGROUND OF THE INVENTION

A keyboard communicates user-entered data to an electronic device, such as a computer. When a user presses a key on the keyboard, the keyboard generates data representative of the particular key that was pressed (e.g., the ASCII code for the letter "e"), and this data is received by a component in the computer, such as a device driver. The device driver then presents the data to whatever program running on the computer is currently receiving input (e.g., by placing the data into the input buffer for whichever application program is active).

One problem that arises in using a keyboard to receive data is when the data is sensitive, or otherwise needs to be kept secret. For example, a secure application (or a secure service of an operating system) may ask the user to enter a password, which should not be generally divulged to the public at large. However, the path leading from the keyboard to the software component that will receive the data is not secure, since there are several opportunities to intercept the data. For example, the data will often travel on a bus that is subject to snooping, and will be handled by a device driver that may be subject to tampering (or that the operating system will allow to be replaced with a non-secure device driver that stores and divulges the information that the driver handles). In other words, there are several opportunities to observe or tamper with secret data on its way from the keyboard to its ultimate destination.

In general, it is possible to encrypt data for transmission between two components that are connected by a non-secure channel. However, many encryption techniques cannot easily be applied in the context of a keyboard, due to various factors, such as key management issues, the possibility of replay attacks, and the fact that the relatively small range of data that can be generated by a keyboard would make an ordinary cipher on keyboard communications relatively easy to break if a moderately-sized sample of ciphertext can be intercepted.

In view of the foregoing, there is a need for a technique that facilitates secure communication with a keyboard.

SUMMARY OF THE INVENTION

The present invention provides a technique for secure communication between two components through a non-secure communication channel. The technique uses an encryption scheme that is particularly well-adapted for a keyboard, and that addresses problems that would exist in applying a standard encryption scheme to a keyboard.

A keyboard in accordance with the invention stores a key and a constant value that is used for initialization of the encryption scheme. A component (e.g., an application running on a computer) stores the same key and the same constant value that are stored at the keyboard. In order to initiate a secure session between the component and the keyboard each generates a nonce, and then exchanges nonce with the other, so that the keyboard and the component are each in possession of both nonces. The keyboard and the component then compute two initial values, each of which is based on the two nonces, the key, and the constant value. For example, the first initial value may be created by using the CBC-3DESMAC algorithm, where CBC-3DESMAC uses the stored constant value as its initial chaining value and applies the key to a message created based on the two nonces. (CBC-3DESMAC refers to applying triple encryption according to the Data Encryption Standard (DES) algorithm with cipher block chaining, and using the final ciphertext block to create a Message Authentication Code (MAC)). Preferably the second initial value is created by inverting the bits in the first initial value (i.e., perform an "exclusive or" operation between the first initial value and the number 0xffffffffffffffff). Since the keyboard and the component compute the first and second initial values in the same way, they are both in possession of the same two initial values.

In an alternative preferred embodiment, the keyboard and the component are equipped with two constant values, and the first and second initial values can be created by applying CBC-3DESMAC to the message that is based on both nonces, using the first constant to create the first initial value, and the second constant to create the second initial value.

After the first and second initial values have been created, the keyboard is ready to communicate encrypted data, and the component that will receive the data is ready to decrypt and verify the data. When data is entered into the keyboard, the keyboard encrypts the data based on the first initial value and the key. Preferably, the keyboard encrypts the data with the above-mentioned key using CBC-3DES (triple-DES with cipher block chaining), with the first initial value being used to prime the cipher block chain. The keyboard also preferably creates a MAC for each unit of data using CBC-3DESMAC, where CBC-3DESMAC applies the above-mentioned key and uses the second initial value to prime the cipher block chain. Preferably, each keystroke is encrypted in a separate encryption block, and the entire stream of data generated at the keyboard during a session constitutes a chain of cipher blocks, since this technique allows the same keystroke (e.g., the letter "e") to appear as different ciphertext depending upon the keystroke that preceded it.

Once the encrypted data and MAC(s) have been received at the receiving component, the receiving component uses the above-mentioned key and the first and second initial values to decrypt and verify the received data.

Other features of the invention are described below.

BRIEF DESCRIPTION OF THE DRAWINGS

The foregoing summary, as well as the following detailed description of preferred embodiments, is better understood when read in conjunction with the appended drawings. For the purpose of illustrating the invention, there is shown in the drawings exemplary constructions of the invention; however, the invention is not limited to the specific methods and instrumentalities disclosed. In the drawings.

DETAILED DESCRIPTION OF THE INVENTION

Exemplary Computing Arrangement

Figure 1:
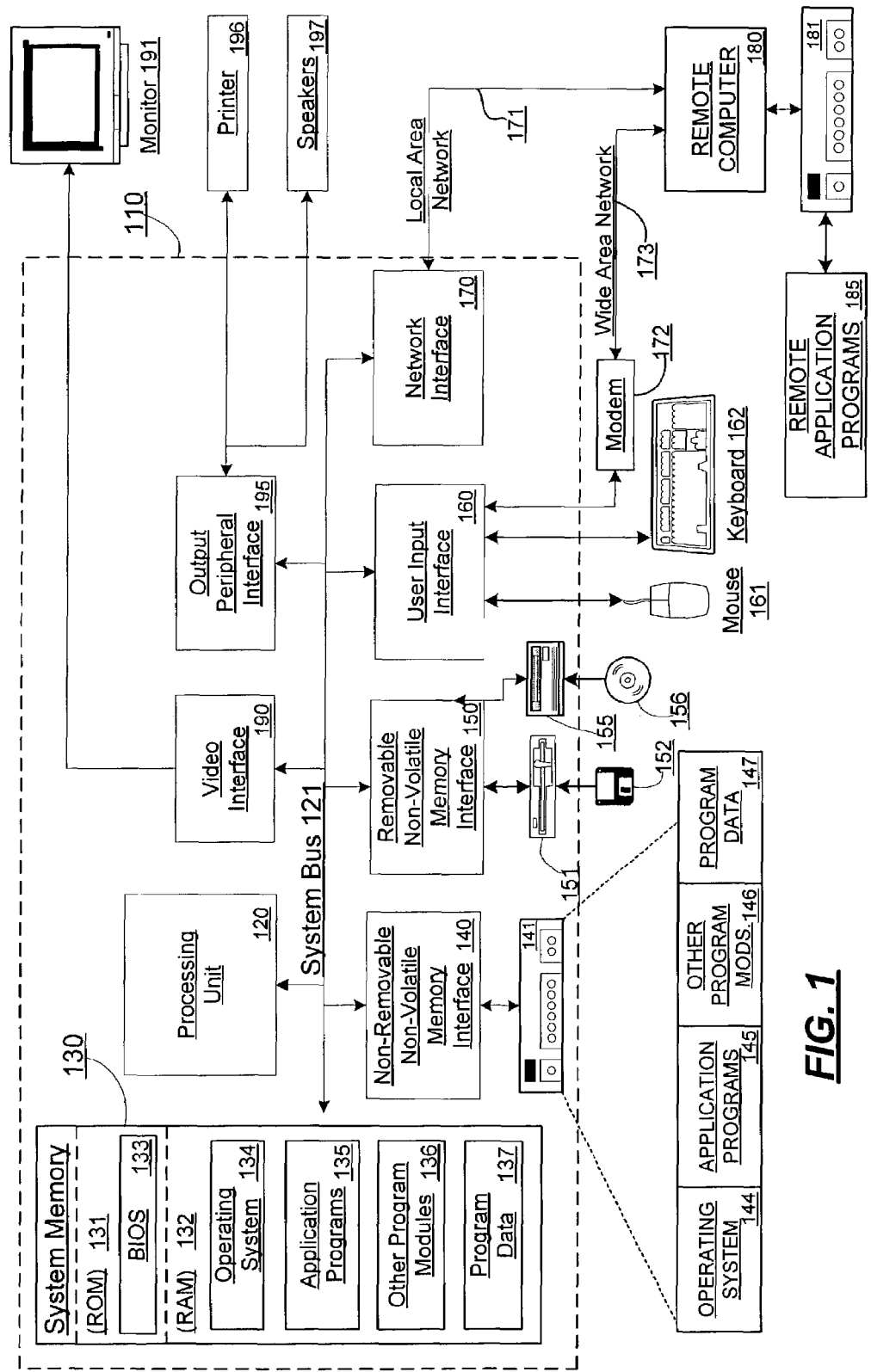
FIG. 1 is a block diagram of an exemplary computing environment in which aspects of the invention may be implemented.

FIG. 1 shows an exemplary computing environment in which aspects of the invention may be implemented. The computing system environment 100 is only one example of a suitable computing environment and is not intended to suggest any limitation as to the scope of use or functionality of the invention. Neither should the computing environment 100 be interpreted as having any dependency or requirement relating to any one or combination of components illustrated in the exemplary operating environment 100.

The invention is operational with numerous other general purpose or special purpose computing system environments or configurations. Examples of well known computing systems, environments, and/or configurations that may be suitable for use with the invention include, but are not limited to, personal computers, server computers, hand-held or laptop devices, multiprocessor systems, microprocessor-based systems, set top boxes, programmable consumer electronics, network PCs, minicomputers, mainframe computers, embedded systems, distributed computing environments that include any of the above systems or devices, and the like.

The invention may be described in the general context of computer-executable instructions, such as program modules, being executed by a computer. Generally, program modules include routines, programs, objects, components, data structures, etc. that perform particular tasks or implement particular abstract data types. The invention may also be practiced in distributed computing environments where tasks are performed by remote processing devices that are linked through a communications network or other data transmission medium. In a distributed computing environment, program modules and other data may be located in both local and remote computer storage media including memory storage devices.

With reference to FIG. 1, an exemplary system for implementing the invention includes a general purpose computing device in the form of a computer 110. Components of computer 110 may include, but are not limited to, a processing unit 120, a system memory 130, and a system bus 121 that couples various system components including the system memory to the processing unit 120. The system bus 121 may be any of several types of bus structures including a memory bus or memory controller, a peripheral bus, and a local bus using any of a variety of bus architectures. By way of example, and not limitation, such architectures include Industry Standard Architecture (ISA) bus, Micro Channel Architecture (MCA) bus, Enhanced ISA (EISA) bus, Video Electronics Standards Association (VESA) local bus, and Peripheral Component Interconnect (PCI) bus (also known as Mezzanine bus).). The system bus 121 may also be implemented as a point-to-point connection, switching fabric, or the like, among the communicating devices.

Computer 110 typically includes a variety of computer readable media. Computer readable media can be any available media that can be accessed by computer 110 and includes both volatile and nonvolatile media, removable and non-removable media. By way of example, and not limitation, computer readable media may comprise computer storage media and communication media. Computer storage media includes both volatile and nonvolatile, removable and non-removable media implemented in any method or technology for storage of information such as computer readable instructions, data structures, program modules or other data. Computer storage media includes, but is not limited to, RAM, ROM, EEPROM, flash memory or other memory technology, CDROM, digital versatile disks (DVD) or other optical disk storage, magnetic cassettes, magnetic tape, magnetic disk storage or other magnetic storage devices, or any other medium which can be used to store the desired information and which can accessed by computer 110. Communication media typically embodies computer readable instructions, data structures, program modules or other data in a modulated data signal such as a carrier wave or other transport mechanism and includes any information delivery media. The term "modulated data signal" means a signal that has one or more of its characteristics set or changed in such a manner as to encode information in the signal. By way of example, and not limitation, communication media includes wired media such as a wired network or direct-wired connection, and wireless media such as acoustic, RF, infrared and other wireless media. Combinations of any of the above should also be included within the scope of computer readable media.

The system memory 130 includes computer storage media in the form of volatile and/or nonvolatile memory such as read only memory (ROM) 131 and random access memory (RAM) 132. A basic input/output system 133 (BIOS), containing the basic routines that help to transfer information between elements within computer 110, such as during start-up, is typically stored in ROM 131. RAM 132 typically contains data and/or program modules that are immediately accessible to and/or presently being operated on by processing unit 120. By way of example, and not limitation, FIG. 1 illustrates operating system 134, application programs 135, other program modules 136, and program data 137.

The computer 110 may also include other removable/non-removable, volatile/nonvolatile computer storage media. By way of example only, FIG. 1 illustrates a hard disk drive 140 that reads from or writes to non-removable, nonvolatile magnetic media, a magnetic disk drive 151 that reads from or writes to a removable, nonvolatile magnetic disk 152, and an optical disk drive 155 that reads from or writes to a removable, nonvolatile optical disk 156, such as a CD ROM or other optical media. Other removable/non-removable, volatile/nonvolatile computer storage media that can be used in the exemplary operating environment include, but are not limited to, magnetic tape cassettes, flash memory cards, digital versatile disks, digital video tape, solid state RAM, solid state ROM, and the like. The hard disk drive 141 is typically connected to the system bus 121 through an non-removable memory interface such as interface 140, and magnetic disk drive 151 and optical disk drive 155 are typically connected to the system bus 121 by a removable memory interface, such as interface 150.

The drives and their associated computer storage media discussed above and illustrated in FIG. 1, provide storage of computer readable instructions, data structures, program modules and other data for the computer 110. In FIG. 1, for example, hard disk drive 141 is illustrated as storing operating system 144, application programs 145, other program modules 146, and program data 147. Note that these components can either be the same as or different from operating system 134, application programs 135, other program modules 136, and program data 137. Operating system 144, application programs 145, other program modules 146, and program data 147 are given different numbers here to illustrate that, at a minimum, they are different copies. A user may enter commands and information into the computer 20 through input devices such as a keyboard 162 and pointing device 161, commonly referred to as a mouse, trackball or touch pad. Other input devices (not shown) may include a microphone, joystick, game pad, satellite dish, scanner, or the like. These and other input devices are often connected to the processing unit 120 through a user input interface 160 that is coupled to the system bus, but may be connected by other interface and bus structures, such as a parallel port, game port or a universal serial bus (USB). A monitor 191 or other type of display device is also connected to the system bus 121 via an interface, such as a video interface 190. In addition to the monitor, computers may also include other peripheral output devices such as speakers 197 and printer 196, which may be connected through an output peripheral interface 190.

The computer 110 may operate in a networked environment using logical connections to one or more remote computers, such as a remote computer 180. The remote computer 180 may be a personal computer, a server, a router, a network PC, a peer device or other common network node, and typically includes many or all of the elements described above relative to the computer 110, although only a memory storage device 181 has been illustrated in FIG. 1. The logical connections depicted in FIG. 1 include a local area network (LAN) 171 and a wide area network (WAN) 173, but may also include other networks. Such networking environments are commonplace in offices, enterprise-wide computer networks, intranets and the Internet.

When used in a LAN networking environment, the computer 110 is connected to the LAN 171 through a network interface or adapter 170. When used in a WAN networking environment, the computer 110 typically includes a modem 172 or other means for establishing communications over the WAN 173, such as the Internet. The modem 172, which may be internal or external, may be connected to the system bus 121 via the user input interface 160, or other appropriate mechanism. In a networked environment, program modules depicted relative to the computer 110, or portions thereof, may be stored in the remote memory storage device. By way of example, and not limitation, FIG. 1 illustrates remote application programs 185 as residing on memory device 181. It will be appreciated that the network connections shown are exemplary and other means of establishing a communications link between the computers may be used.

Security of Communication Between a Keyboard and a Component

Figure 2:
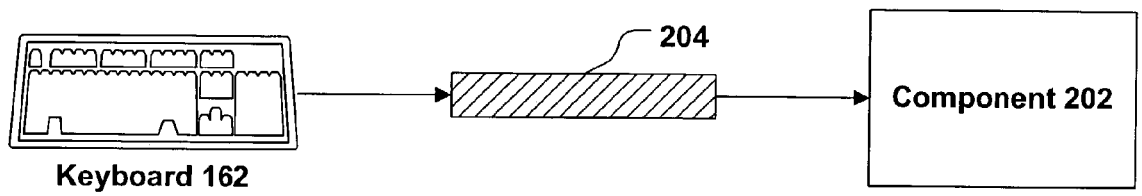
FIG. 2 is a block diagram of a first exemplary environment in which communication between a keyboard and a component may take place over a non-secure channel.

The invention addresses the problem of how a keyboard can be used to communicate securely with a component that requires input from the keyboard. FIG. 2 shows an exemplary scenario of such communication. In FIG. 2, keyboard 162 communicates with component 204. Component 204 can be any type of component—e.g., a program that is executing on a computer, a piece of hardware, etc. Communication from keyboard 162 to component 202 passes through a communication channel that includes at least some non-secure portion 204. That is, as the data that represents keystrokes passes through some channel on its way from keyboard 162 to component 202, there may be some opportunity for a third party to intercept or tamper with the data. This interception or tampering may be a problem if, for example, the information that is being typed at keyboard 162 is a secret password that should not be revealed to the general public.

Figure 3:
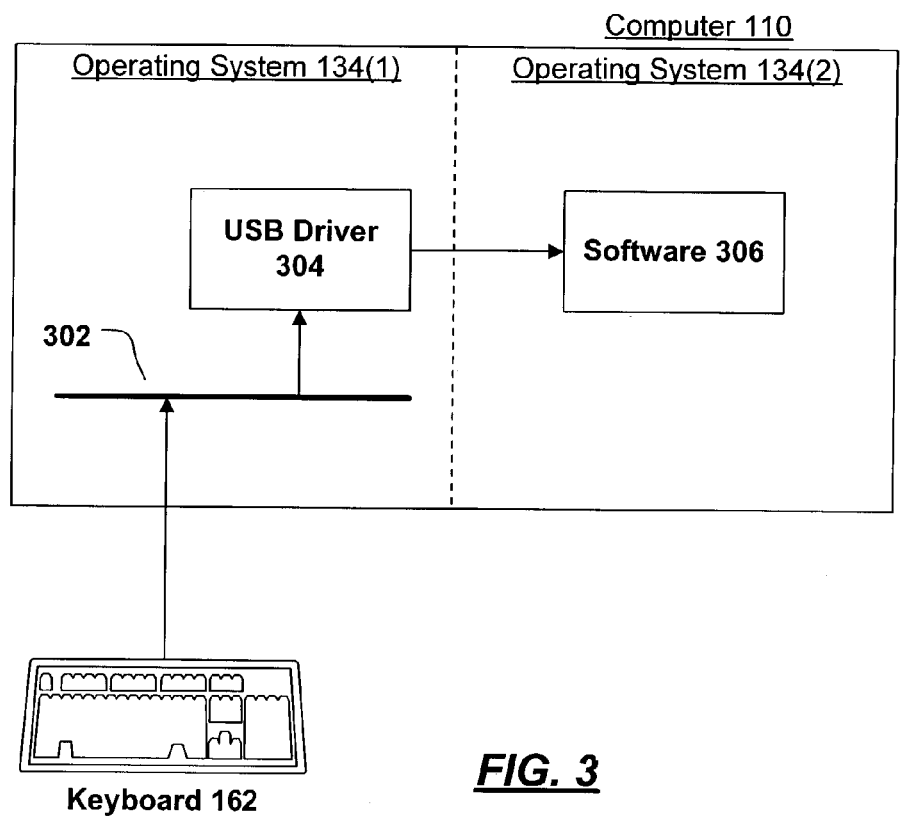
FIG. 3 is a block diagram of a second exemplary environment in which communication between a keyboard and a component may take place over a non-secure channel.

FIG. 3 shows a particular scenario in which secure communication between a keyboard and a component is desired. In FIG. 3, keyboard 162 is used to provide input to software that is running on computer 110. In the example of FIG. 3, keyboard 162 is a keyboard adapted for use with a Universal Serial Bus (USB) 302. (For brevity, such a keyboard shall be referred to as a USB keyboard.) Keyboard 162 receives keystrokes, and places bytes representative of those keystrokes onto USB 302, where the bytes are picked up by USB driver 304. Driver 304 then communicates those bytes to their ultimate destination, which, in the example of FIG. 3, is software 306. Software 306 is an example of component 202 (shown in FIG. 2).

In the example of FIG. 3, there are two operating systems 134(1) and 134(2) running on computer 110. Operating system 134(1) is a typical operating system, such as MICROSOFT WINDOWS XP, Unix, Linux, Solaris, etc. Operating system 134(2) is a "high-assurance" operating system that is used for trusted applications. For example, operating system 134(2) may be associated with a "curtained" memory that is not accessible outside of operating system 134(2), and operating system 134(2) may store secret information (e.g., cryptographic keys, passwords, etc.) in that curtained memory, so that only certain special trusted applications that are permitted to execute under operating system 134(2) are able to read that secret information. Operating system 134(2) is "high assurance" in the sense that the public is entitled to a very high level of assurance that it will perform its function correctly—i.e., if protecting secret information is one of the intended functions of operating system 134(2), the public is entitled to a very high level of assurance that operating system 134(2) will not divulge that secret information. Part of being able protect secret information may include being able to receive typed secrets (e.g., passwords) without divulging these secrets to the outside world. Operating system 134(2) may not trust driver 304 to handle such secret information, since driver 304 is under the control of operating system 134(1) (and operating system 134(1) might allow a hacker to read information directly from USB 302, or substitute a nefarious driver that would store and reveal the secret information). Thus, operating system 134(2) needs a way to receive information from keyboard 162 through operating system 134(1) without concern that the secret information will be divulged by acts arising in operating system 134(1).

It should be understand that while the example of FIG. 3 shows keyboard 162 as communicating with computer 110 through Universal Serial Bus 302, the scenarios described above apply regardless of the exact means by which keyboard 162 communicates with computer 110, and thus the invention is not limited to USB keyboards.

Figure 4:
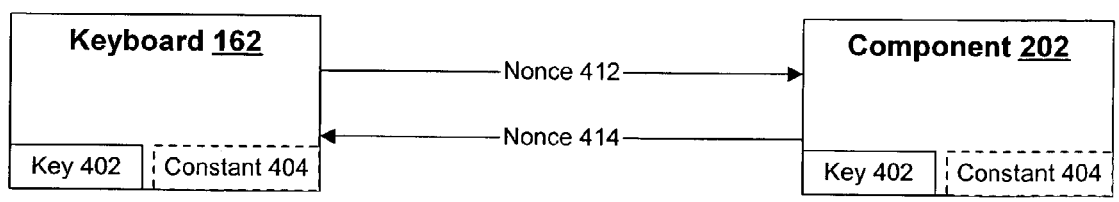
FIG. 4 is a block diagram of a keyboard and a component that have been configured for secure communication, and which exchange nonces, in accordance with aspects of the invention.

FIG. 4 shows how keyboard 162 and component 202 may be configured to participate in secure communication through a non-secure channel. Keyboard 162 and component 202 each store a copy of cryptographic key 402. Keyboard 162 and component 202 also preferably store a constant value 404, which is used as the initial value for a particular preferred cryptographic technique, as more particularly described below. In a further preferred embodiment, keyboard 162 and component 202 may store (in addition to the key) two constant values instead of one; these two constant values may be used in a cryptographic technique as described below. Keyboard 162 may, for example, contain an onboard non-volatile semiconductor that stores key 402 and constant 404, or may have a port that receives a removable storage medium on which key 402 and constant 404 are stored. In the case where component 202 is a software component, key 402 and constant 404 may be stored in component 202's data space. It will be understood, however, that the invention is not limited to any particular manner of storing key 402 and 404.

At the outset of secure communication between keyboard 162 and component 202, keyboard 162 and component 202 may generate and exchange nonces. That is, keyboard 162 generates nonce 412 and sends nonce 412 to component 202. Component 202 generates nonce 414 and sense nonce 414 to keyboard 162. As is known in the art, a nonce is a piece of data that is used in cryptographic applications—often to authenticate an entity cryptographically, or to prime an encryption session with a not-easily-reproduced element on which the encryption can be made dependent. Nonces 412 and 414 may be used to create initial values for encryption and authentication of data transmitted between keyboard 162 and component 202, as more particularly described below.

Process of Securely Sending Data from a Keyboard to a Component

Figure 5:
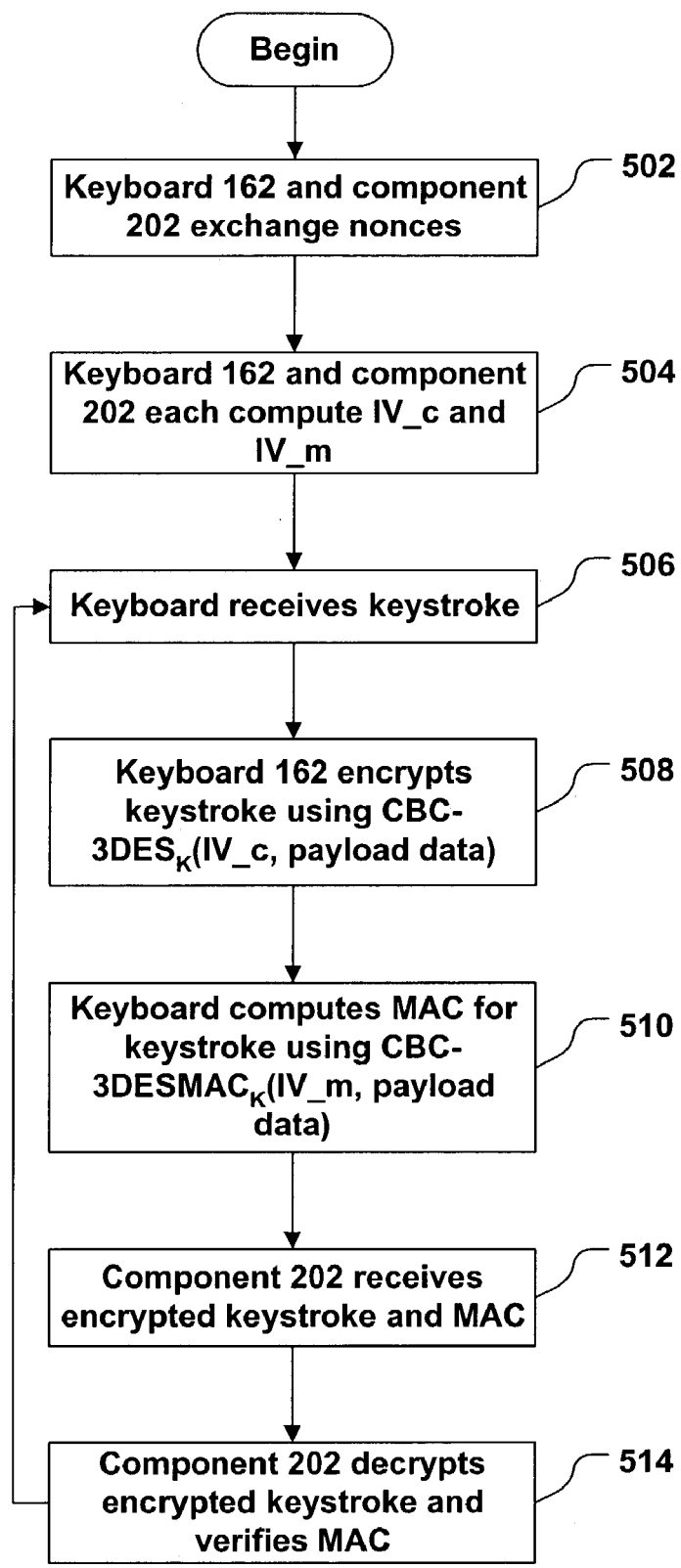
FIG. 5 is a flow diagram of a process for engaging in a secure communication session between a keyboard and a component.

FIG. 5 shows a process by which keyboard 162 and component 202 may engage in a session wherein component 202 securely receives data from keyboard 162. The process of FIG. 5 provides for both encryption (which protects against interception of the transmitted data), and authentication (which protects against modification of the transmitted data). However, it will be understood that either encryption or authentication alone can be used, depending on the security requirements of the transmission. For example, if modification of the data can be tolerated but interception cannot be tolerated, then encryption alone can be used. Conversely, if interception of the data can be tolerated, but modification of the data cannot be tolerated, then authentication alone can be used.

Initially, keyboard 162 and component 202 exchange 502 nonces. For example, as described above in connection with FIG. 4, keyboard 162 may generate nonce 412 and send it to component 202, and component 202 may generate nonce 414 and sent it to keyboard 162. Techniques for generating nonces are known in the art, and thus are not described at length herein. As some examples, nonces 412 and 414 could be generated based on a random number, the contents of some region of memory, time, temperature, phase of the moon, etc., or any other factor that is likely to change often and has a sufficient range that it is unlikely that either keyboard 162 or component 202 will produce the same nonce twice.

After nonces 412 and 414 are exchanged 502, keyboard 162 and component 202 are each in possession of both nonces. Keyboard 162 and component 202 then use a commonly agreed upon formula to compute 504 two initial values—IV_c and IV_m—as functions of both nonces and key 402. That is, if K=key 402, $N_1$=nonce 412, and $N_2$=nonce 414, then IV_c=f(K, $N_1$, $N_2$); and IV_m=g(K, $N_1$, $N_2$).

The functions f and g can be any functions. In a preferred embodiment, f(K, $N_1$, $N_2$)=CBC-3DESMAC$_K$(const_IV, $N_1$|$N_2$); and g(K, $N_1$, $N_2$)=f(K, $N_1$, $N_2$) xor 0xffffffffffffffff, where const_IV is equal to constant value 404 (shown in FIG. 4). In a further preferred embodiment, where the keyboard and the component share two constant values (e.g., const_IV_1 and const_IV_2), the functions f and g can alternatively be computed as follows:

f(K, $N_1$, $N_2$)=CBC-3DESMAC$_K$(const_IV_1, $N_1$|$N_2$); and g(K, $N_1$, $N_2$)=CBC-3DESMAC$_K$(const_IV_2, $N_1$|$N_2$), (The operator "|" means concatenation, so that $N_1$|$N_2$ is the value resulting from concatenating $N_1$ with $N_2$. "xor" is the bitwise "exclusive or" operation, such that A xor B is the value resulting from setting to "1" any bit that is a "1" in either A or B but not both, and setting all other bits to zero.) CBC-3DESMAC$_K$(const_IV, $N_1$|$N_2$) is a cryptographic function, whose meaning is known in the art and described in greater detail below.

After IV_c and IV_m have been computed, communication between keyboard 162 and component 202 can begin. Keyboard 162 receives a keystroke—i.e., by an operator pressing one of the keys (or certain combinations of keys, such as <SHIFT> and "A", or <CTRL> and "A") (step 506). The keyboard next encrypts 508 the keystroke; the encryption is preferably based on key 402 and IV_c. In a preferred embodiment, the keystrokes are encrypted using CBC-3DES, with key 402 as the key and IV_c as the initial value. CBC-3DES is a cryptographic algorithm that is known in the art and described in greater detail below below. Additionally, keyboard 162 computes 510 a message authentication code (MAC) for the keystroke, preferably based on key 402 and IV_m. In a preferred embodiment, the message authentication code is created using CBC-3DESMAC, with key 402 as the key and IV_m as the initial value. As noted above, CBC-3DESMAC is known in the art and described in greater detail below.

After the keyboard has created both the encrypted keystroke data and the MAC, component 202 receives 512 the encrypted keystroke data and MAC from keyboard 162 (step 512). Component 202 then decrypts 514 the data using key 402 and IV_c, and also verifies the data using key 402 and IV_m (step 514). The process then returns to step 506 to receive the next entry at the keyboard.

The Cryptographic Functions CBC-3DES and CBC-3DES-MAC

CBC-3DES is a cryptographic function that combines the data encryption standard (DES) with cipher block chaining (CBC). "3DES" means that the DES encryption algorithm is applied to a given block of data three times ("triple-DES"). DES encrypts data by applying a key to the data in a known manner. DES encrypts a long message by dividing the message into smaller blocks, and encrypting the individual blocks. (When "triple-DES" is used, the DES algorithm is applied to each block three times in order to produce the ciphertext for that block.) DES (and triple-DES) can encrypt each block of data using just a key; however, when cipher block chaining is used, the encryption of one block is based not only on the key, but also on the ciphertext that was produced by encrypting the last block. Thus, encryption of a given block is based on two inputs: the key, and the ciphertext that resulted from encrypting the previous block. Since the first block of data to be encrypted has no "previous" block, the cipher block chaining process must be primed with an "initial value"—that is, the first block of data is encrypted based on the key and some initial value. The initial value is not used in the encryption of subsequent blocks, but may indirectly influence how those blocks are encrypted (since the first block's ciphertext is based on the initial value, the second block's ciphertext is based on the first block's ciphertext, and so on).

In view of the preceding discussion, the phrase "CBC-$3DES_K$(IV, message)," means encrypting "message" with the key K, using triple-DES and cipher block chaining, where IV is the initial value for the cipher block chain.

CBC-3DESMAC is a way of using CBC-3DES to produce a message authentication code (MAC). In particular, the phrase CBC-$3DESMAC_K$(IV, message) means that "message" is encrypted with a key K using triple-DES and cipherblock chaining, and using IV as the initial value for the cipher block chain. However, since the goal of CBC-3DES-MAC is only to produce a MAC for the message instead of a complex ciphertext for the message, only the last block of ciphertext is saved, and the remaining blocks of ciphertext may be discarded. This last block of ciphertext may be used as a MAC, since—even given a constant key and a constant IV—different messages are unlikely to produce the same final block (or, more precisely, if each block can represent $2^n$ different values, there is only a 1 in $2^n$ chance that any two messages will have the same final block).

It should be noted that the particular choice of CBC-3DES, as well as the way in which it is used, particularly advantageous for encrypted keyboard communication. Since the domain of messages to be encrypted is small (e.g., on the order of 128 different ASCII characters), cipher block chaining is particularly useful in keeping the cipher from being broken. If straight encryption were used (without chaining), then, within a given session, each character would encrypt to the same ciphertext each time it was typed—e.g., typing an "e" would always produce the same ciphertext. By making an educated guess (e.g., by using the fact that "e" is the most commonly occurring letter in the English language), one could more easily break such a cipher. Chaining all of the input in a session makes the cipher harder to break by ensuring that the same data may appears as different ciphertext depending upon where it appears in the input stream (e.g., an "e" may not always produce the same ciphertext). Additionally, changing the encryption for each session by creating a new initial value based on nonces prevents observers from detecting patterns of usage that they could use to compromise security (e.g., if the first text typed in every session is the password, an observer could capture the ciphertext for the password and institute a replay attack). Moreover, the size of cipher blocks used by DES is particularly well suited, since DES operates on 8-byte blocks, and most keyboard protocols transmit data in blocks that can fit into this size (E.g., the USB standard also deals in 8-byte blocks, so each USB block can fit into one DES block with no wasted space.) However, it should be understood that any other block cipher could be used, and chaining concepts similar to CBC could be applied to such a block cipher.

It should further be noted that, for the same reasons that the encryption scheme described herein is particularly well-suited to a keyboard, that encryption scheme is also well suited to certain other types of input devices, such as a mouse (or other pointing device). These input devices share various features in common with a keyboard, such as a small vocabulary, and a limited ability to execute a complicated encryption algorithm.

Exemplary Use of Keyboard that Encrypts Data

Figure 6:
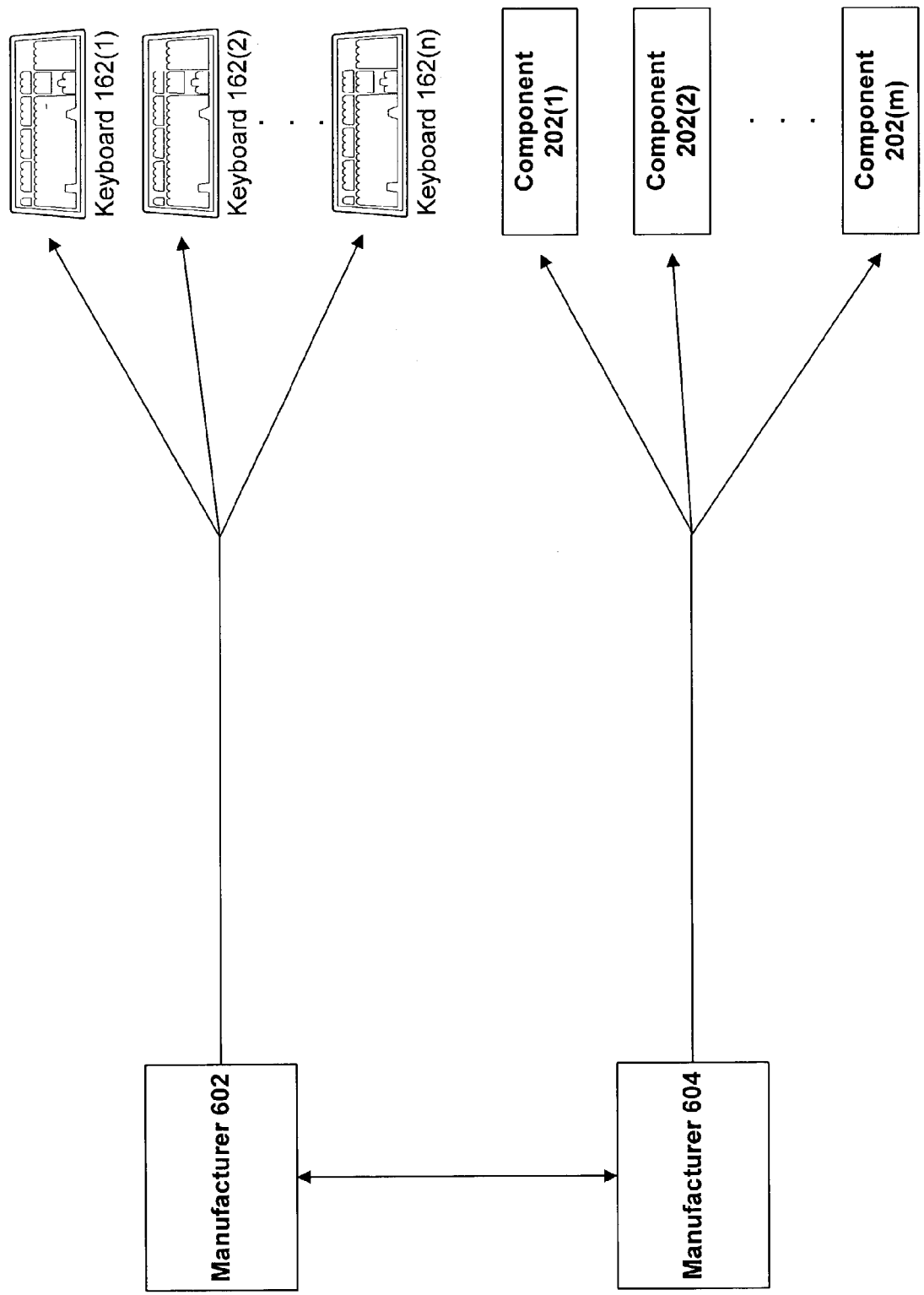
FIG. 6 is a block diagram of a first exemplary environment in which keyboards and components may be distributed to engage in secure communication according to aspects of the invention.

FIG. 6 shows an exemplary environment in which a keyboard that performs encryption may be used with components that require secure communication. In the example of FIG. 6 manufacturer 602 manufactures a plurality of keyboards 162(1), 162(2), . . . , 162(n), and distributes these keyboard for public use. Each of the keyboard 162(1), 162(2), . . . , 162(n) incorporates key 402 and constant value 404 (shown in FIG. 4) (or incorporates some means by which key 402 and constant value 404 can be accessed externally, such as by means of a port for a removable semiconductor memory). Manufacturer 604 produces components 202(1), 202(2), . . . , 202(m) that benefit from securely communicating with a keyboard. Each of components 202(1), 202(2), . . . , 202(n) incorporates key 402 and constant value 404 (or is somehow able to receive the key and constant value). Components 202(1), 202(2), . . . , 202(m) may now receive input from keyboards 162(1), 162(2), . . . , 162(n), through the techniques described above.

Manufacturer 602 may have a preexisting relationship with manufacturer 604, so that both manufacturers can agree on a key 402 and a constant 404 that should be incorporated for secure communication. In one example manufacturers 602 and 604 are the same entity. In another example, manufacturer 604 is a manufacturer of components 202(1), 202(2), . . . , 202(m), who would like those components to be able to receive data from secure keyboards, and manufacturer 602 is a manufacturer of keyboards, whom manufacturer 604 has deemed sufficiently trustworthy to manufacture keyboards for secure communication with components 202(1), 202(2), . . . , 202(m), and to hold key 402 and/or constant 404.

It is noted that the foregoing examples have been provided merely for the purpose of explanation and are in no way to be construed as limiting of the present invention. While the invention has been described with reference to various embodiments, it is understood that the words which have been used herein are words of description and illustration, rather than words of limitations. Further, although the invention has been described herein with reference to particular means, materials and embodiments, the invention is not intended to be limited to the particulars disclosed herein; rather, the invention extends to all functionally equivalent structures, methods and uses, such as are within the scope of the appended claims. Those skilled in the art, having the benefit of the teachings of this specification, may effect numerous modifications thereto and changes may be made without departing from the scope and spirit of the invention in its aspects.

What is claimed:

1. A method of communicating with a keyboard comprising:

receiving, at a component, a first nonce from the keyboard;

sending from the component a second nonce to the keyboard; and creating a first initial value and a second initial value by applying triple-DES and cipher block chaining to a combination of said first nonce and said second nonce, using a key and a third initial value that is known both to the keyboard and to the component;

receiving, at the component from the keyboard, a plurality of data that have been encrypted with triple-DES and cipher block chaining using said key and said first initial value, each separate keystroke received from said keyboard being included within a separate one of plurality of data, each one of the plurality of data being encrypted using a separate block of said triple-IDES and cipher block chaining, said key and sad first initial value being known both to the component and to the keyboard;

decrypting the plurality of data based on the first initial value and the key.

2. The method of claim 1, further comprising:
receiving at the component from the keyboard, a plurality of message authentication codes corresponding to the plurality of data, said message authentication codes having been created with triple-DES and cipher block chaining using said key and a second initial value different from said first initial value, said second initial value being known both to the component and to the keyboard;
verifying the plurality of data by using the plurality of message authentication codes.

3. The method of claim 2, further comprising:
receiving a first nonce from the keyboard;
sending a second nonce to the keyboard;
creating the first initial value by applying triple-DES and cipher block chaining to a combination of the first nonce and the second nonce, using the key and a third initial value that is known both to the keyboard and to the component; and
creating the second initial value by applying triple-DES and cipher block chaining to a combination of the first nonce and the second nonce, using the key and a fourth initial value that is known both to the keyboard and to the component.

4. The method of claim 1, wherein the plurality of data are received through a channel whose behavioral integrity is not trusted by the component.

5. The method of claim 4, wherein the component comprises a first operating system which executes on a computing device along with a second operating system, the first operating system distrusting, in at least some respect, the behavior of the second operating system, the keyboard communicating with the first operating system through a driver controlled by the second operating system.

6. The method of claim 1, wherein the keyboard comprises a USB keyboard.

7. The method of claim 6, wherein said triple-DES and cipher block chaining encrypt data in blocks having a predetermined size, and wherein the keyboard communicates data in blocks of said predetermined size.

8. The method of claim 1, further comprising:
receiving a first nonce from the keyboard;
sending a second nonce to the keyboard; and
creating the first initial value by applying triple-DES and cipher block chaining to a combination of the first nonce and the second nonce, using the key and a second initial value that is known both to the keyboard and to the component.

9. A computer-readable medium encoded with computer-executable instructions to perform a method of securely receiving input at a component from a keyboard, the method comprising:
receiving at the component a first nonce from the keyboard;
sending from the component a second nonce to the keyboard, and
creating a first initial value and a second initial value by applying triple-DES and cipher block chaining to a combination of said first nonce aid said second nonce, using a key and a third initial value that is known both to the keyboard and to the component;
receiving, at the component from the keyboard, a plurality of encrypted keystrokes, the encrypted keystrokes having been created at the keyboard by encrypting input keystrokes received at the keyboard with triple-DES and cipher block chaining using the key and the first initial value, each individual one of the plurality of keystrokes being encrypted using a separate block of said triple-DES and cipher block chaining, the key and the first initial value being available both to the keyboard and to the component; and
at the component, decrypting the plurality of encrypted keystrokes using the key and the first initial value.

10. The computer-readable medium of claim 9, wherein the component comprises a first operating system which executes on a computing device along with a second operating system, the first operating system distrusting, in at least some respect, the behavior of the second operating system, the keyboard communicating with the first operating system through a driver controlled by the second operating system.

11. The computer-readable medium of claim 9, wherein the method further comprises:
receiving at the component from the keyboard, a plurality of message authentication codes corresponding to the plurality of encrypted keystrokes, said message authentication codes having been created with triple-DES and cipher block chaining using said key and a second initial value different from said first initial value, said second initial value being known both to the component and to the keyboard;
verifying the plurality of encrypted keystrokes by using the plurality of message authentication codes.

12. The computer-readable medium of claim 11, wherein the method farther comprises:
receiving a first nonce from the keyboard;
sending a second nonce to the keyboard;
creating the first initial value by applying triple-DES and cipher block chaining to a combination of the first nonce and the second nonce, using the key and a third initial value that is known both to the keyboard and to the component; and
creating the second initial value applying triple-DES and cipher block chaining to a combination of the first nonce and the second nonce, using the key and a fourth initial value that is known both to the keyboard and to the component.

13. The computer-readable medium of claim 9, wherein said triple-DES and cipher block chaining encrypt data in blocks having a predetermined size, and wherein the keyboard communicates data in blocks of said predetermined size.

14. A keyboard comprising:
One or more storage locations that store a first initial value and a key;
an encryption component that is adapted to receive a first nonce from the recipient through the communication interface, to send a second nonce to the recipient through the communication interface, and to create the first initial value by applying triple-DES and cipher block chaining to a combination of the first nonce and the second nonce, using the key and a second initial value that is known both to the keyboard and to the component, wherein said encryption component encrypts input data received at the keyboard with triple-DES and cipher block chaining using said key and said first initial value, whereby encrypted data is created based on said input data, each individual one of said input data being representative of a separate keystroke received at said keyboard each of said individual ones of said input data being encrypted using a separate block of said triple-DES and cipher block chaining; and a communication interface that communicates said encrypted data to a device external to the keyboard, said encrypted data being destined for a recipient that knows said first initial value and said key.

15. The keyboard of claim 14, wherein the encryption component further creates a plurality of message authentication codes corresponding to the encrypted data or the input data, said message authentication codes having been created with triple-DES and cipher block chaining using said key and a second initial value different from said first initial value.

16. The keyboard of claim 14, wherein the keyboard comprises a USB keyboard.

17. The keyboard of claim 14, wherein the communication interface communicates said encrypted data to a driver that is controlled by a first operating system that executes on said device whereupon said encrypted data is communicated to said recipient, said recipient being a second operating system that executes on said device or a program that executes under said second operating system, said second operating system distrusting, in at least some respect, the behavior of the first operating system.

18. A computer-readable medium encoded with computer-executable instructions to perform a method of enabling a keyboard to engage in a secure communication with a component external to the keyboard, the method comprising:

sending a first nonce to the component;

sending a second nonce to the component; and creating a first initial value by applying triple-DES and cipher block chaining to a combination of the first nonce and the second nonce using a key and a second initial value that is known both to the keyboard and to the component, receiving a plurality of input keystrokes;

encrypting each of the input keystrokes with triple-DES and cipher block chaining using the key and the first initial value, each one of the input keystrokes being encrypted using a separate block of said triple-DES and cipher block chaining, the key and the first initial value being known to both the keyboard and the component; and transmitting the encrypted keystrokes to the component.

19. The computer-readable medium of claim 18, wherein said triple-DES and cipher block chaining encrypt data in blocks having a predetermined size, and wherein the keyboard communicates data in blocks of said predetermined size.

20. The computer-readable medium of claim 18, wherein the method further comprises:

creating a plurality of message authentication codes with triple-DES and cipher block chaining using said key and a second initial value different from said first initial value, the plurality of message authentication codes corresponding to the plurality of keystrokes; and transmitting the message authentication codes to the component.

21. A method of enabling data to be inputted securely to a software component comprising:

distributing a copy of the software component, the software component comprising:

a key;

an first initial value; and computer-executable instructions that enable the software to:

send a first nonce to a keyboard;

receive a second nonce from the keyboard;

create a second initial value based on said first nonce, said second nonce, and said first initial value; and decrypt encrypted data received from the keyboard using the key and the second initial value; and distributing, or enabling the distribution of, the keyboard, the keyboard comprising:

hardware to store or access a copy of the key;

hardware to store or access a copy of the first initial value;

hardware or software that enables the keyboard to:

receive the first nonce from the software component;

send the second nonce to the software component; and create the second initial value based on said first nonce, said second nonce, and said first initial value; and create the encrypted data by encrypting input data received at the keyboard using the key and the second initial value, wherein each individual one of said input data is representative of a separate keystroke on said keyboard, each of said individual ones of said input data being encrypted using a separate block of triple-DES and cipher block chaining.

22. The method of claim 21, wherein said keyboard further comprises hardware or software that enables the keyboard to:

create a third initial value based on said first nonce, said second nonce, and said first initial value, said third initial value being different from said second initial value; and create a message authentication code using the key and the third initial value;

the software component further comprises computer-executable instructions to:

create said third initial value based on said first nonce, said second nonce, and said first initial value; and verify the message authenticate code using the key and the third initial value.

* * * * *